(12) United States Patent
Moldt et al.

(10) Patent No.: US 6,376,673 B1
(45) Date of Patent: Apr. 23, 2002

(54) PIPERIDINE DERIVATIVES AS NEUROTRANSMITTER RE-UPTAKE INHIBITORS

(75) Inventors: Peter Moldt; Frank Watjen; Jorgen Scheel-Kruger, all of Ballerup (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 09/415,227

(22) Filed: Oct. 12, 1999

Related U.S. Application Data

(63) Continuation of application No. PCT/DK98/00185, filed on May 12, 1998.

(30) Foreign Application Priority Data

May 14, 1997 (DK) ................................................ 0553/97

(51) Int. Cl.$^7$ ...................... C07D 211/18; C07D 211/26
(52) U.S. Cl. ........................................ 546/229; 546/232
(58) Field of Search .................................. 546/232, 229

(56) References Cited

U.S. PATENT DOCUMENTS

| | | | | |
|---|---|---|---|---|
| 4,048,165 A | * | 9/1977 | Weitz et al. ................. | 546/232 |
| 4,927,837 A | | 5/1990 | Galliani et al. .............. | 546/232 |

FOREIGN PATENT DOCUMENTS

| | | |
|---|---|---|
| EP | 0367393 A2 | 5/1990 |
| WO | WO 97/09311 A1 | 3/1997 |

\* cited by examiner

Primary Examiner—Alan L. Rotman
Assistant Examiner—Raymond Covington
(74) Attorney, Agent, or Firm—Birch, Stewart, Kolasch & Birch, LLP

(57) ABSTRACT

The present invention relates to compounds of formula (I), or a pharmaceutically acceptable salt thereof; wherein R is hydrogen, alkyl, alkenyl, alkynyl, cycloalkyl, cycloalkylalkyl or 2-hydroxyethyl; $R^3$ is —CR'=NOR" wherein R' and R" each independently are hydrogen, alkyl, cycloalkyl, cycloalkylalkyl, alkenyl, cycloalkylalkenyl, alkynyl, cycloalkylalkynyl, aryl or benzyl; $R^4$ is phenyl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl; 3,4-methylenedioxyphenyl; benzyl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl; heteroaryl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl; or naphthyl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl. The compounds possess valuable pharmaceutical properties as monoamine neurotransmitter, i.e. dopamine, serotonin, noradrenaline, reuptake inhibitors.

(I)

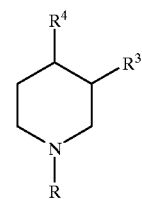

7 Claims, No Drawings

PIPERIDINE DERIVATIVES AS NEUROTRANSMITTER RE-UPTAKE INHIBITORS

This application is a continuation of PCT/DK98/00185 filed May 12, 1998. The entire contents of which are hereby incorporated by reference.

The present invention relates to novel piperidine-derivatives which are valuable monoamine neurotransmitter, i.e dopamine, serotonin and noradrenaline, re-uptake inhibitors and the use of the novel piperidine derivatives for the treatment of disorders or diseases responsive to the inhibition of monoamine neurotransmitter re-uptake, including diseases such as Parkinson's disease, depression, obsessive compulsive disorders, panic disorders, dementia, memory deficits, attention deficit hyperactivity disorder, obesity, anxiety, eating disorders and drug addiction or misuse, including cocaine abuse.

BACKGROUND OF THE INVENTION

The brain consists of a plurality of neurons that communicate with each other via chemical messengers. Each neuron generates neurochemicals or neurotransmitters which act at sites being referred to as receptors on the cellular membrane of neurons. One group. of neurotransmitters, referred to as the monoamine neurotransmitters, includes serotonin, dopamine and noradrenaline.

Monoamine neurotransmitters are released into the synaptic cleft between neurons in order to stimulate postsynaptic receptor activity. The removal (or inactivation) of monoamine neurotransmitters occurs mainly by a reuptake mechanism into the presynaptic terminals. By inhibiting the re-uptake an enhancement of the physiological activity of monoamine neurotransmitters occur.

The compounds of the present invention are valuable monoamine reuptake inhibitors, in particular dopamine reuptake inhibitors, and are as such considered useful for the treatment of Parkinsonism, depression, obesity, narcolepsy, drug addiction or misuse, including cocaine abuse, attention-deficit hyperactivity disorders, Gilles de la Tourettes disease and senile dementia. Dopamine re-uptake inhibitors enhances indirectly via the dopamine neurones the release of acetylcholin and are therefore also useful for the treatment of memory deficits, e.g. in Alzheimers disease, presenile dementia, memory dysfuntion in ageing, and chronic fatigue syndrome.

Compounds with noradrenaline re-uptake inhibiting activity are considered useful for enhancing attention, alertness, arousal, vigilance and for treating depression.

The serotonergic neural system of the brain have been shown to influence a variety of physiologic functions, and compounds having serotonin re-uptake inhibiting activity are predicted to have the ability to treat in mammals, including humans, a variety of disorders associated with this neural system, for example eating disorders, depression, obsessive compulsive disorders, panic disorders, alcoholism, pain, memory deficits and anxiety.

The compounds of the present invention are valuable inhibitors of serotonin reuptake and therefore predicted to be useful for the treatment of a range of disorders as mentioned above. Included among these disorders are depression and disorders related to depression, such as pseudodementia or Ganser's syndrome, migraine pain, bulimia, obesity, premenstrual syndrome or late luteal phase syndrome, tobacco abuse, panic disorder, post-traumatic syndrome, memory loss, dementia of ageing, memory dysfunction in ageing, social phobia, attention deficit hyperactivity disorder, chronic fatigue syndrome, premature ejaculation, erectile difficulty, anorexia nervosa, disorders of sleep, autism, mutism or trichotillomania.

OBJECTS OF THE INVENTION

It is an object of the present invention to provide novel piperidine-derivatives which are monoamine neurotransmitter re-uptake inhibitors and therefore useful for the treatment of disorders such as Parkinson's disease, depression and related diseases, obsessive compulsive disorders, panic disorders, dementia, memory deficits, attention deficit hyperactivity disorder, obesity, anxiety, eating disorders, drug addiction or misuse, including cocaine abuse.

Another object of the present invention is to provide novel pharmaceutical compositions containing the novel piperidine-derivatives.

Still another object of the invention is to provide a method of treating diseases or disorders responsive to the inhibition of monoamine neurotransmitter re-uptake, such as Parkinsonism, depression and related diseases, obsessive compulsive disorders, panic disorders, dementia, memory deficits, attention deficit hyperactivity disorder, obesity, anxiety, eating disorders, drug addiction or misuse, including cocaine abuse.

Other objects will become apparent hereinafter to one skilled in the art.

THE PRESENT INVENTION

The invention then, inter alia, comprises the following, alone or in combination:

A compound having the formula,

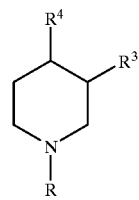

or a pharmaceutically acceptable salt thereof; wherein

R is hydrogen, alkyl, alkenyl, alkynyl, cycloalkyl, cycloalkylalkyl or 2-hydroxyethyl;

$R^3$ is —CR'=NOR" wherein R' and R" each independently are hydrogen, alkyl, cycloalkyl, cycloalkylalkyl, alkenyl, cycloalkylalkenyl, alkynyl, cycloalkylalkykyl, aryl or benzyl;

$R^4$ is phenyl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl;

3,4-methylenedioxyphenyl;

benzyl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl;

heteroaryl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl; or naphthyl which may be substituted one or more times with substituents selected from the group consisting of halogen, $CF_3$, CN, amino, nitro, alkoxy, cycloalkoxy, alkyl, cycloalkyl, alkenyl, alkynyl, aryl and heteroaryl;

a compound as above which is

1-Metyl-3-methoxyiminomethyl-4-(3,4-dichlorophenyl) piperidine or a pharmaceutically acceptable addition salt thereof;

a pharmaceutical composition, comprising a therapeutically effective amount of a compound as above, or a pharmaceutically acceptable addition salt thereof, together with at least one pharmaceutically acceptable carrier or diluent;

the use of a compound as above for the manufacture of a medicament for the treatment of a disorder or disease of a living animal body, including a human, which disorder or disease is responsive to the inhibition of monoamine neurotransmitter re-uptake in the central nervous system;

the use of a compound as above for the manufacture of a medicament for the treatment of a disorder or disease of a living animal body, including a human, which disorder or disease is responsive to the inhibition of dopamine neurotransmitter re-uptake in the central nervous system;

the use of a compound as above wherein the disorder or disease is Parkinsonism, depression, pseudodementia, obesity, narcolepsy, drug addiction and/or abuse, attention-deficit hyperactivity disorders, senile dementia, or memory dysfunction;

a method for the preparation of the compounds as above comprising the step of reacting a compound having the formula

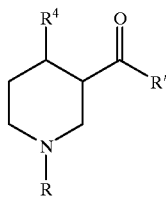

herein $R^4$, R' and R is as defined above, with a compound having the formula $NH_2$—OR", wherein R" is as defined above;

a method of treating a disorder or disease of a living animal body, including a human, which disorder or disease is responsive to the inhibition of monoamine neurotransmitter reuptake, comprising the step of administering to such a living animal body, including a human, in need thereof a therapeutically effective amount of a compound as above;

a method of treating a disorder or disease of a living animal body, including a human, which disorder or disease is responsive to the inhibition of dopamine neurotransmitter reuptake, comprising the step of administering to such a living animal body, including a human, in need thereof a therapeutically effective amount of a compound as above; and the methods as above, wherein Parkinsonism, depression, pseudodementia, obesity, narcolepsy, drug addiction and/or abuse, attention-deficit hyperactivity disorders cognitive dysfunction, senile dementia, or memory dysfunction is treated.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Cycloalkylalkyl means cycloalkyl as above and alkyl as above, meaning for example, cyclopropylmethyl.

Alkenyl means a group of from two to six carbon atoms, including at least one double bond, for example, but not limited to ethenyl, 1,2- or 2,3-propenyl, 1,2-, 2,3-, or 3,4-butenyl.

Cycloalkylalkenyl means cycloalkyl as above and alkenyl as above.

Alkynyl means a group of from two to six carbon atoms, including at least one triple bond, for example, but not limited to ethynyl, 2,3-propynyl, 2,3- or 3,4-butynyl.

Cycloalkylalkenyl means cycloalkyl as above and alkynyl as above.

Alkoxy is O-alkyl, wherein alkyl is as defined above.

Cycloalkoxy is O-cycloalkyl, wherein cycloalkyl is as defined above.

Amino is $NH_2$ or NH-alkyl or N-(alkyl)$_2$, wherein alkyl is as defined above.

Heteroaryl is a 5- or 6-membered heterocyclic monocyclic group. Such an heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl and 3-pyrazinyl and 1-pyrazolyl, 3-pyrazolyl, and 4-pyrazolyl.

Aryl is an aromatic hydrocarbon, such as phenyl and naphthyl.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxytic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the reservation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

The compounds of the invention may be prepared in numerous ways. The compounds of the invention and their pharmaceutically acceptable derivatives may thus be prepared by any method known in the art for the preparation of compounds of analogous structure, and as shown in the representative examples which follow.

The following scheme illustrates one method by which the compounds of the invention can be prepared:

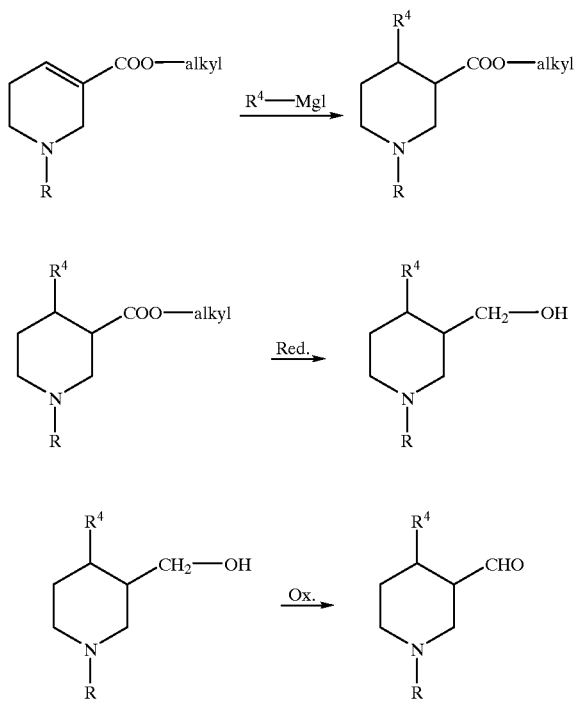

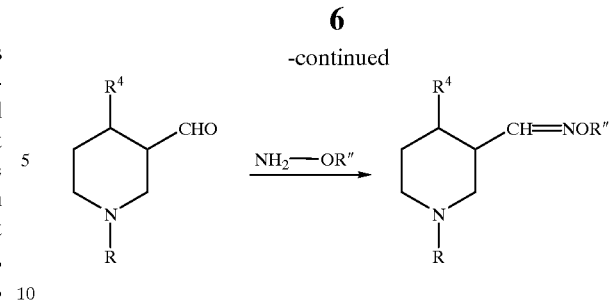

Starting materials for the processes described in the present patent application are known or can be prepared by known processes from commercially available materials.

A compound of the invention can be converted to another compound of the invention using conventional methods.

The products of the reactions described herein are isolated by conventional means such as extraction, crystallization, distillation, chromatography, and the like.

Biology

The compounds of the present invention have been tested for their ability to bind to the dopamine transporter in the following tests for in vitro inhibition of $^3$H-WIN 35428.

In vitro Inhibition of $^3$H-WIN 35428 Binding

Background

Dopamine transporters/uptake sites on nerve terminals presumably function to terminate neuronal signaling by removing dopamine from the synaptic cleft. The activity or presence of the dopamine transporter integral protein can be measured in vitro with synaptosomal uptake of $^3$H-dopamine or membrane binding assays with $^3$H-ligands known to bind to the transporter.

In vitro binding studies of cocaine have demonstrated that cocaine binds to the dopamine transporter and inhibits $^3$H-dopamine uptake. Numerous ligands of several structural types have been reported to bind at the dopamine uptake site, but it remains questionable whether their binding sites are identical to that of cocaine. A structural analog og cocaine, $^3$H-WIN 35428, binds selectively and with high affinity to the dopamine transporter complex.

Tissue preparation: Preparations are performed at 0–4° C. unless otherwise indicated. Corpus striatum from male Wistar rats (150–200 g) is homogenized for 5–10 sec in 10 ml $NaH_2PO_4$ (50 mM, pH 7.4) using an Ultra-Turrax homogenizer. The suspension is centrifuged at 27,000×g for 15 min. The supernatant is discarded and the pellet is resuspended in 50 mM $NaH_2PO_4$, pH 7.4 (1000 ml per g of original tissue) and used for binding assays.

Assay: Aliquots of 0.5 ml tissue are added to 25 ml of test solution and 25 ml of $^3$H-WIN 35428 (1 nM, final concentration), mixed and incubated for 60 min at 2° C. Non-specific binding is determined using cocaine (30 mM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

25–75% inhibition of specific binding must be obtained, before calculation of an $IC_{50}$. The test value is given as $IC_{50}$ (the concentration ($\mu$M) of the test substance which inhibits the specific binding of $^3$H-WIN 35428 by 50%).

The results obtained by testing a compound of the invention are given in the following table:

TABLE 1

| Test Compound | In Vitro $IC_{50}$ μM |
|---|---|
| 1-methyl-3-methoxyiminomethyl-4-(3,4-dichlorophenyl)piperidine | 0.016 |

The test result presented above show that the test compound according to the invention binds with high affinity to the dopamine transporter complex.

Compounds of the present invention have also been tested for their ability to inhibit reuptake of dopamine(DA) noradrenaline(NA) and serotonin(5-HT) in synaptosomes.

Background

Specific neurotransmitter transporters/uptake sites on nerve terminals presumably function to terminate neuronal signaling by removing the neurotransmitters dopamine, noradrenaline and serotonin, respectively, from the synaptic cleft. The activity of the transporter integral proteins can be measured in vitro by synaptosomal uptake of $^3$H-dopamine, $^3$H-noradrenaline and $^3$H-serotonin, respectively.

In vitro Inhibition of $^3$H-dopamine ($^3$H-DA) Uptake in Striatal Synaptosomes Tissue preparations: Preparations are performed at 0–4° C. unless otherwise indicated. Corpi striati from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-DA (1 nM, final concentration), mixed and incubated for 25 min at 37° C. Non-specific uptake is determined using benztropine (10 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$. The test value is given as $IC_{50}$ (the concentration (μM) of the test substance which inhibits the specific binding of $^3$H-DA by 50%).

In vitro Inhibition of $^3$H-noradrenaline ($^3$H-NA) Uptake in Hippocampal Synaptosomes Tissue preparation: Preparations are performed at 0–4° C. unless otherwise indicated. Hippocampi from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (2000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM MgSO4, 0.97 mM $CaCl_2$, 10 mM glucose and 1 mM ascorbic acid.

Assay: Aliquots of 4.0 ml tissue suspension are added to 100 μl of test solution and 100 μl of $^3$H-NA (1 nM, final concentration), mixed and incubated for 90 min at 37° C. Non-specific uptake is determined using desipramine (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-NA by 50%).

In vitro Inhibition of $^3$H-5-hydroxytryptamine ($^3$H-5-HT, Serotonin) Uptake in Cortical Synaptosomes Tissue preparation: Preparations are performed at 0–4° C. unless otherwise indicated. Cerebral cortices from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-5-HT (1 nM, final concentration), mixed and incubated for 30 min at 37° C. Non-specific uptake is determined using citalopram (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-5-HT by 50%).

Test results obtained by testing a compound of the invention appear from the table below:

Table 2

| Test compound | DA-uptake IC$_{50}$(nM) | NA-uptake IC$_{50}$(nM) | 5-HT-uptake IC$_{50}$(nM) |
|---|---|---|---|
| 1-methyl-3-methoxyimino-4-(3,4-dichlorophenyl)piperidine | 0.024 | 0.014 | 0.12 |

The result presented above show that the compounds tested efficiently inhibits reuptake of dopamine, noradrenaline and serotonin in synaptosomes.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of the present invention are useful in the treatment of disorders or diseases responsive to the inhibition of monoamine neurotransmitter re-uptake. The monoamine reuptake inhibiting activity of the compounds of the invention make them extremely useful in the treatment of, parkinsonism, depression, obesity, narcolepsy, drug abuse, e.g cocaine misuse, attention-deficit hyperactivity disorders, senile dementia and cognitive dysfunction as well as other disorders sensitive to monoamine neurotransmitter reuptake-inhibiting activity. The compounds of the invention may accordingly be administered to a living animal body, including a human, in need of treatment, alleviation, or elimination of an indication associated with or responsive to compounds having monoamine neurotransmitter uptake-inhibiting activity. This includes especially parkinsonism, depression, obesity, narcolepsy, cocaine abuse, attention-deficit hyperactivity disorders, senile dementia and memory dysfunction in ageing.

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

I.p. means intraperetoneally, which is a well known route of administration. P.o. means peroral, which is a well known route of administration.

The following examples will illustrate the invention further, however, they are not to be construed as limiting.

EXAMPLE 1

1-Methyl-3-methoxycarbonyl-4-(3,4-dichlorophenyl)piperidine

To magnesium (5.5 g, 229 mmol) and a few crystals of iodine in anhydrous ether (20 mL) was added 3,4-dichlorobromobenzene (46.4 g, 206 mmol) in anhydrous ether (200 mL) at a rate sufficient to keep the reaction at reflux. After the addition was completed the reaction was heated at reflux for another 15 min. The reaction was cooled to −20° C. and arecoline (16 g, 103 mmol) in anhydrous ether (200 mL) was added over 20 min while keeping the temperature at −20° C. The reaction was stirred for another 2 hour at −20° C. and then heated to 0° C. Hydrochloric acid (4 N, 80 mL) was added and the pH adjusted to 1 using concentrated hydrochloric acid. The organic phase was separated off and the pH adjusted to 9 with concentrated ammonia. Extraction with ether (2×200 mL)afforded 24.6 g of the title compound as a brownish oil.

EXAMPLE 2

1-Methyl-3-hydroxymethyl-4-(3,4-dichlorophenyl)piperidine

To a solution of 1-methyl-3-methoxycarbonyl-4-(3,4-dichlorophenyl)piperidine (10 g, 33 mmol) in tetrahydrofuran (100 mL) at −20° C. was added a suspension of lithium aluminium hydride (1.2 g, 32 mmol) in tetrahydrofuran (150 mL) over 35 min. The reaction was heated to 0° C. followed by successive addition of water (1 mL), sodium hydroxide (4 N, 1 mL) and water (10 mL). The reaction was stirred for another 30 min and filtered through celite. Evaporation of the solvent afforded 9.3 g of the title compound as an oil.

EXAMPLE 3

1-Methyl-3-formyl-4-(3,4-dichlorophenyl)piperidine

To a solution of oxalyl chloride (3.3 mL, 37.9 mmol) in methylene chloride (100 mL) cooled below −40° C. was added dimethyl sulfoxide (5.6 mL, 79 mmol) in methylene chloride (5 mL). The reaction was stirred for another 30 min at −40° C. and 1-methyl-3-hydroxymethyl-4-(3,4-dichlorophenyl)piperidine (9.0 g, 33 mmol) in methylene chloride (100 mL) was added over 15 min while keeping the temperature below −40 ° C. The reaction was stirred for another 30 min at this temperature and then allowed to heat to room temperature. Water (100 mL) was added and the organic phase separated off. The aqueous phase was extracted with methylene chloride (2×100 mL). The combined organic extracts were dried over magnesium sulphate and evaporated to dryness to give 10 g of the title compound.

EXAMPLE 4

1-Metyl-3-methoxyiminomethyl-4-(3,4-dichlorophenyl)piperidine

To a solution of 1-methyl-3-formyl-4-(3,4-dichlorophenyl)piperidine (10 g, 33 mmol) in warm isopropanol (100 mL) was added methoxylamine hydrochloride (3 g, 36 mmol). The reaction was heated at reflux for 30 min. The solvent was evaporated off and the residue made basic (pH=9) using concentrated ammonia. Extraction with ether afforded 8.5 g of crude product. Purification by repeated column chromatography on silica using EtOAc/Et$_3$N (95:5) as eleuent afforded 4 g of the title compound as an oil.

What is claimed is:

1. A compound having the formula,

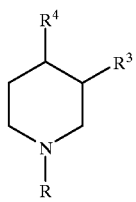

or a pharmaceutically acceptable salt thereof; wherein
R is hydrogen, alkyl, alkenyl, alkynyl, cycloalkyl, cycloalkylalkyl or 2-hydroxyethyl;
R$^3$ is —CR'=NOR" wherein R' and R" each independently are hydrogen, alkyl, cycloalkyl, cycloalkylalkyl, alkenyl, cycloalkylalkenyl, alkynyl, cycloalkylalkylnyl, aryl or benzyl;
R$^4$ is
phenyl which may be substituted one or more times with substituents selected from the group consisting of halogen, CF$_3$, CN, amino, nitro, alkoxy, cycloalkoxy, alkyl, cycloalkyl, alkenyl, alkynyl, aryl and heteroaryl;
3,4-methylenedioxyphenyl;
benzyl which may be substituted one or more times with substituents selected from the group consisting of halogen, CF$_3$, CN, amino, nitro, alkoxy, cycloalkoxy, alkyl, cycloalkyl, alkenyl, alkynyl, aryl and heteroaryl;
heteroaryl selected from the group consisting of oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 3-pyrazinyl, 1-pyrazolyl, 3-pyrazolyl, and 4-pyrazolyl, which heteroaryl may be substituted one or more times with substituents selected from the group consisting of halogen, CF$_3$, CN, amino, nitro, alkoxy, cycloalkoxy, alkyl, cycloalkyl, alkenyl, alkynyl, aryl and heteroaryl; or
naphthyl which may be substituted one or more times with substituents selected from the group consisting of halogen, CF$_3$, CN, amino, nitro, alkoxy, cycloalkoxy, alkyl, cycloalkyl, alkenyl, alkynyl, aryl and heteroaryl.

2. A compound of claim 1 which is
1-Metyl-3-methoxyiminomethyl-4-(3,4-dichlorophenyl) piperidine
or a pharmaceutically acceptable addition salt thereof.

3. A pharmaceutical composition, comprising a therapeutically effective amount of a compound of claims 1 to 2, or a pharmaceutically acceptable addition salt thereof, together with at least one pharmaceutically acceptable carrier or diluent.

4. A method for the preparation of the compounds according to claim 1 comprising the step of reacting a compound having the formula

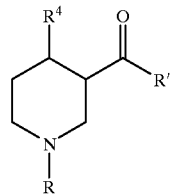

wherein R$^4$, R' and R is as defined in claim 1, with a compound having the formula NH$_2$—OR", wherein R" is as defined in claim 1.

5. A method of treating a disorder or disease of a living animal body, including a human, which disorder or disease is responsive to the inhibition of monoamine neurotransmitter reuptake, comprising the step of administering to such a living animal body, including a human, in need thereof a therapeutically effective amount of a compound according to claims 1 to 2.

6. A method of treating a disorder or disease of a living animal body, including a human, which disorder or disease is responsive to the inhibition of dopamine neurotransmitter reuptake, comprising the step of administering to such a living animal body, including a human, in need thereof a therapeutically effective amount of a compound according to claims 1 to 2.

7. The method of claim 5, wherein parkinsonism, depression, pseudodementia, obesity, narcolepsy, drug addiction and/or abuse, attention-deficit hyperactivity disorders cognitive dysfunction, senile dementia, or memory dysfunction is treated.

* * * * *